United States Patent [19]
Gagnieu

[11] Patent Number: 5,412,076
[45] Date of Patent: May 2, 1995

[54] CROSSLINKABLE COLLAGEN DERIVATIVES, PROCESS FOR THEIR PRODUCTION AND THEIR APPLICATION TO THE PREPARATION OF BIOMATERIALS

[75] Inventor: Christian Gagnieu, Chassieu, France

[73] Assignee: Flamel Technologies, Venissieux Cedex, France

[21] Appl. No.: 77,605

[22] Filed: Jun. 17, 1993

[30] Foreign Application Priority Data

Jun. 18, 1992 [FR] France .................. 92 07692

[51] Int. Cl.$^6$ .............. A61K 37/12; A61K 9/70; C07K 13/00; A61L 15/32
[52] U.S. Cl. ................... 530/356; 106/124; 106/125; 602/42; 602/43; 602/48; 602/50; 424/443; 424/444; 424/445; 424/484
[58] Field of Search ............ 530/356; 106/124, 125; 602/42, 43, 48, 50; 424/443, 444, 445, 484

[56] References Cited

U.S. PATENT DOCUMENTS

| 4,294,241 | 10/1981 | Miyata | 602/50 |
| 4,407,787 | 10/1983 | Stemberger | 424/444 |
| 5,219,895 | 6/1993 | Kelman et al. | 522/68 |

FOREIGN PATENT DOCUMENTS

| 49469 | 4/1982 | European Pat. Off. . |
| 191994 | 8/1986 | European Pat. Off. . |
| 330389 | 8/1989 | European Pat. Off. . |
| 2238051 | 5/1991 | United Kingdom . |

*Primary Examiner*—Michael G. Wityshyn
*Assistant Examiner*—Nancy J. Gromet
*Attorney, Agent, or Firm*—Bacon & Thomas

[57] ABSTRACT

The present invention relates to a crosslinkable modified collagen which is soluble in water and/or in aprotic polar organic solvents and which contains free or substituted thiol groups carried by residues of cysteine or derivatives thereof, at least some of the residues being fixed to the collagen via spacer compounds. It further relates to processes for the production of the collagen. Applications are adhesives, biomaterials for prostheses, implants, or other medical articles.

16 Claims, No Drawings

CROSSLINKABLE COLLAGEN DERIVATIVES, PROCESS FOR THEIR PRODUCTION AND THEIR APPLICATION TO THE PREPARATION OF BIOMATERIALS

The present invention relates to novel crosslinkable collagen derivatives capable of being used in the preparation of biomaterials from which it is possible to obtain products applicable especially in medicine, and more particularly in surgery, or in cosmetology.

Among these products, there may be mentioned artificial tissues or organs such as artificial skin, bone, ligament, cardiovascular, intraocular and other prostheses or implants, or else encapsulation systems (implants, microspheres, microcapsules) for the controlled release of active principles in vivo, and bioencapsulation systems.

Examples which may also be mentioned are medical accessories such as suture threads or coverings for rendering implantable medical articles biocompatible, as well as injectable collagen solutions or suspensions used for making up and reconstructing tissues.

For each of the biomedical applications mentioned above, it is essential to obtain certain physicochemical, mechanical or biological properties for the crosslinked collagen in reproducible and controlled ways. Only perfect control over the chemical modifications of the collagen, the large range of products synthesized according to the invention and the good adaptability of the crosslinking processes which result therefrom make it possible satisfactorily to comply with the majority of the constraints which become apparent when the specification sheet of a given application is drawn up.

The invention further relates to a process for the production of these novel crosslinkable collagen derivatives, to novel intermediates involved in the above-mentioned process and, finally, to the crosslinked collagen produced from the crosslinkable collagen in question.

The field of the invention is that of biocompatible collagen-based materials which are useful as starting materials for making articles to be placed in contact with, or implanted in, the human or animal body, and which are capable of mimicking biological materials as well as possible, especially from the mechanical point of view, so as to be able to replace them. The intended application is essentially human or veterinary medicine.

Collagen is a known protein which is present at every level of the organization of animal tissues: it is the principal protein of skin and connective tissue. By nature, it possesses biochemical and physicochemical characteristics which are relatively well adapted to the living environment.

As far as the present invention is concerned, the term collagen denotes any peptide of a collagen nature, including gelatin in particular.

Different grades of collagen of animal or human origin are currently marketed throughout the world, essentially for the preparation of biomaterials or cosmetic products.

The properties of the different grades available are regarded as adequate in the applications which are in general use at the present time.

Thus these collagens include excellent supports for cell adhesion, multiplication and growth, which are of value in the production of cell culture media.

Benefit is also derived from their hydrophilicity, their low immunogenicity and their hemostatic character.

The mechanical properties of native collagens are acceptable for a number of uses.

However, it has to be accepted that, in the field of implantable medical articles such as implants and prostheses, commercial native collagens suffer from substantial deficiencies in respect of their mechanical strength and their resistance to proteolysis.

In fact, the introduction of these foreign bodies, which is what implants and prostheses are, into a living organism induces rejection phenomena which give rise especially to inflammatory reactions; these cause inter alia the production of collagenase, which hydrolyzes the collagen. The consequence of this is at least a degradation of the mechanical behavior of the collagen-based graft.

It is known that crosslinking makes it possible to improve the mechanical properties of collagen. It gives the collagen fibers a very high tensile strength and tear strength by virtue of the numerous covalent bonds which it creates between the collagen chains.

On the basis of this scientific knowledge, numerous studies have been undertaken to develop the possibilities of the artificial crosslinking of collagen.

Thus three major types of technique for crosslinking this protein have appeared.

The first type of technique is crosslinking with the aid of a bridging agent, where exogenous molecules, which are most often bifunctional, are grafted so that bonds can be established. The reagents most frequently employed are:

Mono- and di-aldehydes such as formaldehyde (generating methylene bridges), malonaldehyde and especially glutaraldehyde (crosslinking by way of imine and aldol bonds). The main problems are due to their terminal —CHO groups, which are irritant, and to the autopolymerization of dialdehydes, which renders them cytotoxic.

Dicarboxylic compounds, which have so far been employed essentially either for modifying collagen or for tanning skins, and which act by way of amide or ester bonds.

Diamines such as hexamethylenediamine, which act solely by way of amide bonds.

Diisocyanates, including hexamethylene diisocyanate, which is used for crosslinking by way of amide bonds.

Disulfonyl chlorides, which establish intra- and intercatenary bonds.

A second type of technique involves the creation of a network by means of covalent bonding between the collagen molecules, without the grafting of exogenous compounds.

The main methods employed are:

Irradiation (ultraviolet or gamma radiation), which produces a number of oxidative deaminations permitting crosslinking by way of imine and aldol bonds, and at the same time very reactive free radicals capable of creating covalent bridging structures. Such a method has the disadvantage of causing the collagen to crosslink only in a narrow zone at low energies, whereas at high energies it results in hydrolysis or denaturation reactions which are very detrimental to the product.

Dehydration (under harsh conditions: above 100° C., under vacuum), which leads to the formation of amide and ester bonds as well as intra- and intermolecular lysinoalanines. Carbodiimides, such as cyanamide or dicyclohexylcarbodiimide, may be mentioned among the reagents employed. This mode of crosslinking is still at the experimental stage.

Enzymatic crosslinking by means of proteins mimicking the effect of lysyl oxidase (enzyme responsible for natural crosslinking). This method is still being studied at the present time.

Oxidation-reduction, which induces oxidative deamination of the terminal amino groups, which become aldehyde groups. This is done using essentially metal cations ($Cu^{2+}$, $Fe^{2+}$, $Al^{3+}$) in association with cofactors (ascorbate, pyridoxal 5-P), as well as sulfites or nitrites. This method is very widely used for tanning leather.

Functional activation of the carboxyls in particular, which can produce acid azides having a very selective reactivity towards the terminal —$NH_2$ groups and leading to the formation of an amide bond. A variety of biomaterials can be made in this way.

The third type of technique is crosslinking by copolymerization. This consists in combining the collagen with another polymer by means of covalent bonds to give more or less interlocked conformations. The polymers most often associated with the collagen are:

acrylic derivatives, the toxicity of which is often incompatible with applications in human medicine of the implant type, acrylonitrile/styrene mixtures, which have so far failed to get beyond the laboratory stage, polyurethanes, which are used especially in the strengthening of tanned leather, polyalcohols, and silicones.

The bonds involved in the copolymerization are very diverse and depend on the groups which each polymer possesses.

All these techniques, whether of a physical or chemical nature, have numerous disadvantages.

First of all, chemical crosslinking reactions give rise to toxic residues in the crosslinked collagen. The residues can be in the form of unconsumed reagents or of free reactive groups coming from bifunctional reagents which have only reacted at one end.

Physical crosslinking reactions are all difficult to carry out and lack reproducibility.

In general, these two types of crosslinking result in a partial or total loss of the affinity of the tissue cells for the modified collagen.

Moreover, they cannot be used to obtain molded articles from collagen solutions. In fact, none of them enables either the kinetics of crosslinking or the degree of crosslinking to be controlled.

Under such random conditions, it is not possible to envisage simple and economic industrial manufacturing processes which give products of a mechanical quality suited to the intended applications.

It is for this reason that, in the large majority of cases, crosslinking techniques have been used to a limited extent on anatomical parts or tissues containing collagen.

More exceptionally, they have been used for the crosslinking of preformed collagen articles, essentially films or felts.

In any case, they are still ineffectual in the broad remaining area of applications as biomaterials.

It has been proposed elsewhere to exploit the bridging structure most commonly encountered in biological systems: the disulfide bond —S—S—.

Thus the article entitled "Einbau von Cystin-Brücken in Kollagen" ("Incorporation of cystine bridges in collagen")—F. SCHADE & H. ZAHN—Angew. Chem. 74, 904 (1962), has described the direct fixing of a cystine derivative in collagen, without a spacer intermediate, in an attempt to effect crosslinking by way of an —S—S— bridging structure.

In this brief summary of their studies, the authors claim to have obtained collagen crosslinked by disulfide bridges.

The crosslinking agent used is a cystine derivative in which the two amine groups of the cystine have been blocked by a protecting group of the carbobenzoxy type.

After grafting on to the collagen, the disulfide bridges were reduced and then reoxidized with atmospheric oxygen (autocrosslinking factor) in a basic medium.

This article teaches the direct grafting of cystine on to collagen without the use of a spacer compound.

Twenty years after this first article, European patent application no. 0 049 469 discloses a dressing based on a combination of collagen and fibrinogen. Said document describes the direct introduction of thiol groups into soluble collagen extracted from tendons. The thiol groups are introduced via N-acetylhomocysteine thiolactone without a spacer compound joining it to the collagen.

One object of the present invention is to propose a crosslinkable modified collagen which is soluble in water and/or in aprotic polar organic solvents, carries free or substituted thiol groups belonging to residues of cysteine or analogs thereof, and is capable of crosslinking in these media, by the formation of disulfide bridges, to give gels or crosslinked products in the presence of mild oxidizing agents, affording excellent control over the kinetics and the degree of crosslinking.

A further object of the invention is to provide a "thiolized" collagen which can be converted to gels or crosslinked products whose crosslinking density, and hence mechanical strength, can be modulated in advance so as to be adaptable to any application.

A further object of the invention is to provide a crosslinkable modified collagen whose flexibility and crosslinking performance characteristics make it a particularly appropriate starting material for the production, for example by molding or extrusion, of solid medical articles of the medical implant or prosthesis type.

Therefore, after having carried out numerous experiments and studies, the Applicant has succeeded in overcoming the obstacles with which the prior art was confronted, and in achieving these and other objects by fixing at least some of the cysteic residues to the collagen via spacer compounds.

Thus the present invention relates to a novel crosslinkable modified collagen which is soluble in water and/or in aprotic polar organic solvents and which contains free or substituted thiol groups carried by residues of cysteine or derivatives thereof, at least some of said residues being fixed to the collagen via spacer compounds.

In totally advantageous manner, the modified collagen according to the invention is easy to shape and manipulate on the industrial scale. It makes it possible to obtain medical articles of the implant, prosthesis or artificial skin type which are non-toxic and non-immunogenic and whose mechanical and biological properties are perfectly suited to the intended application.

As far as the present invention is concerned, the term "crosslinkable" arbitrarily denotes modified collagens capable of autocrosslinking spontaneously in the presence of atmospheric oxygen, at room temperature, if appropriate in the presence of mild auxiliary agents, such as oxidizing agents, which are not directly involved in the reaction and do not end up in the crosslinked product.

The excellent biocompatibility of this modified collagen originates in part from the fact that the free or substituted thiol groups are carried by residues of cysteine or analogs thereof (hereafter arbitrarily denoted by the general term "cysteic" residues), for example cysteine itself, cystine, homocysteine, homocystine, cystamine and cysteamine.

According to the invention, at least some of the "cysteic" residues are bonded to the collagen via spacer compounds. Each spacer compound preferably comprises several carboxyl radicals. Even more preferably, the spacer compound is a hydrocarbon unit of a carboxylic nature which preferably comes from a dicarboxylic acid capable of forming a cyclic anhydride. The dicarboxylic acid in question can be selected from the following non-limiting list: succinic, glutaric, phthalic, itaconic and maleic acids, succinic acid being particularly preferred.

This spacer compound enables at least some of the "cysteic" residues to be grafted indirectly on to the collagen amino acids containing free alcohol or amine groups. Other "cysteic" residues fix directly to the amino acids carrying carboxyl groups (glutamic and aspartic acids).

The degree of substitution of the modified collagen according to the invention by free thiol groups can vary over a wide range of values.

This modified collagen is easily converted to the crosslinked state by oxidation of the thiol groups and the creation of disulfide bridges in a mild oxidizing environment. Under physiological conditions, in vivo, this can take place by autooxidation with dissolved oxygen or by enzymatic oxidation, whereas under non-physiological conditions, in vitro, oxidation can be effected with the aid of reagents which are nontoxic at the active doses, such as hydrogen peroxide or atmospheric oxygen, e.g. in a weakly basic medium.

The crosslinked polymer can be obtained in a form which is very stable and possesses good mechanical properties.

The invention further relates, by way of a novel product, to a crosslinked collagen which is insoluble especially in water and/or in organic solvents and whose intercatenary bridging structures are formed at least partially by disulfide bridges obtained from the cysteic residues fixed to the collagen, and at least partially via spacer compounds.

The latter can be of the same type as those described above.

This crosslinked collagen can be obtained from the autocrosslinkable modified collagen referred to above.

The present invention further relates to a process for the production of a crosslinkable modified collagen which is soluble in water and/or in aprotic polar organic solvents and which contains free thiol groups.

This process consists essentially in reacting the starting collagen:
method I:
either with the precursor of the spacer compound in a first stage and then with a cysteic residue in a second stage,
method II:
or with a reaction subunit consisting of at least the spacer compound bonded to at least one cysteic residue.

The successive steps of method I are as follows:
$a_1$—solubilization of the starting collagen in at least one aprotic polar organic solvent,
$b_1$—acylation and carboxylation of the solubilized collagen,
$c_1$—activation of the free carboxyl groups of the collagen, and
$d_1$—reaction of the activated collagen with a cysteic residue containing a blocked thiol group or groups and, if appropriate, a blocked carboxyl group or groups, to give an inert precursor of the intended modified collagen.

In a first mode of carrying out method I of the process according to the invention, provision is made for an additional step $e_1$ consisting in the direct activation of the inert precursor by the formation of free or substituted thiol groups, giving the intended crosslinkable modified collagen. This activation can be carried out especially by reduction.

In a second mode of carrying out method I of the process according to the invention, provision is made for the following additional steps:
$e_{11}$—indirect activation of the inert precursor, preferably by oxidation, giving collagen crosslinked via intercatenary disulfide bridges, and
$f_{11}$—conversion of the crosslinked collagen, preferably by reduction, to modified collagen carrying stabilized free or substituted thiol groups.

Steps $a_1$ to $d_1$, $e_1$, $e_{11}$ and $f_{11}$ are described in detail below.

Using method II, the process comprises essentially the following successive steps:
$a_2$—solubilization of the starting collagen in at least one polar organic solvent,
$b_2$—preparation of the spacer compound/cysteic residue subunit containing protected thiol groups,
$c_2$—activation of the free carboxyl groups of the subunit, and
$d_2$—reaction of the collagen with the activated subunit to give an inert precursor of the intended modified collagen.

To obtain the latter, it suffices to carry out an additional step $e_2$, which consists in a reduction to give collagen-SH.

In one alternative, step $d_2$ can be followed by steps $e_{21}$ and $f_{21}$, which are identical to steps $e_{11}$ and $f_{11}$ described above.

Steps $a_2$ to $e_2$, $e_{21}$ and $f_{21}$ are described in greater detail below.

The starting material used in this process can be animal or human collagen of any type, preferably of type I and/or III or IV, which is solubilizable in aprotic polar organic solvents, may or may not contain telopeptides and is employed in denatured form (single chains) or non-denatured form (triple helix).

Said collagen can optionally be a collagen modified for example by acylation (e.g. succinylation) of its amino groups, or else by conversion to the salt of an acid, for example succinic acid.

It is self-evident that the starting material can consist of one or more of these different types of collagen.

In step $a_1$ or $a_2$, the starting collagen is solubilized in an aprotic polar organic solvent such as dimethyl sulfoxide (DMSO), dimethylacetamide (DMAC), dimethylformamide (DMF) or N-methylpyrrolidone (NMP).

This solubilization is preferably effected with the help of a solubilization aid, which can be a solvent, for example methanol, or a carboxylic acid preferably corresponding to that employed in step b.

If the starting collagen contains telopeptides, it can be subjected to an appropriate preliminary reduction, alkalization, acidification and precipitation treatment known per se. The aim of this treatment is to increase the solubility of said collagen in the solvent of step $b_1$.

Step $b_1$ is a step for acylation and carboxylation of the solubilized collagen. It is preferably carried out with the aid of the anhydride of a dicarboxylic acid. This reaction enables one of the terminal COOH groups of the diacid to be fixed by covalent bonding to a free OH or $NH_2$ group of the amino acids. Finally, the peptide chain carries free COOH groups which each consist of the other terminal carboxyl group of the diacid.

As the reactive form is to take the form of an anhydride, the dicarboxylic acid is selected from those which are capable of forming cyclic anhydrides. Diacids containing at least 4 carbon atoms are preferred.

The following list of compounds may be mentioned by way of example: succinic, glutaric, phthalic, itaconic, citraconic and maleic acids. This list should of course be extended to cover all types of derivatives of the above-mentioned acids.

Succinic and glutaric anhydrides are particularly preferred.

Advantageously, the anhydride is reacted with the collagen in solution in the presence of an organic base, preferably of the tertiary type, such as triethylamine or else N-methylmorpholine or N-ethylmorpholine.

After extraction and washing, a collagen is recovered which is substituted by the diacid in question to a degree which can be modulated as a function of the proportion of anhydride brought into contact with the collagen, and/or as a function of the amount of base used.

In general, taking into account the number of reactive groups available on the collagen, the degree of substitution can be as much as about 22 acylated amino acids per hundred amino acids of the collagen, preferably 4 to 22. These acylated collagens, for example succinylated collagens, which preferably have a degree of substitution of between 4 and 22 acyl radicals per hundred amino acids, constitute novel stable intermediates.

The substituted collagens obtained are soluble in water at a pH above 5.5-7 and in aprotic polar organic solvents, irrespective of the anhydride used.

By way of illustration and without implying a limitation, it can be indicated that the collagens substituted by succinic acid are soluble in water at a pH below 2.3 and above 5.5.

After acylation/carboxylation, the collagens contain between about 10 and 30% by number of amino acid residues carrying a carboxyl group. These are firstly the amino acid residues which have reacted with the acid anhydride, and secondly the glutamic acid and aspartic acid present in the starting collagen.

In method II, step $b_2$ consists in preparing a reaction subunit, namely spacer compound/cysteic residue or spacer compound/cysteic residue/spacer compound.

The cysteic residue is preferably of the type described above, having at each end a dicarboxylic acid radical such as those mentioned previously, for example a disuccinylcystamine.

Step $c_1$ for activation of the carboxyl groups of the carboxylated collagen, and step $c_2$ for activation of the reactive subunit, are advantageously carried out:
either with a carboxylic acid halide, preferably an acid chloride, leading to the formation of mixed anhydrides on every free carboxyl group of the acylated collagen or of the reactive subunit,
or with carbonyldiimidazole.

In the case where an acid chloride is used, it is generally selected from the family of the alkyl and/or aryl chlorocarbonates and the chlorides of bulky carboxylic acids.

The preferred choice will be ethyl chloroformate or else trimethylacetyl chloride.

The activation is performed in a polar aprotic solvent medium (DMSO, DMF, DMAC or NMP, by itself or in a mixture), preferably in the presence of a tertiary organic base such as triethylamine, N-methylmorpholine or N-ethylmorpholine, triethylamine being preferred.

In the case of carbonyldiimidazole, the activation is performed in an aprotic polar solvent medium (without organic base).

As regards the collagen, this activation reaction affects not only the carboxyl residues introduced in step $b_1$, but also the carboxyls of the glutamic and aspartic amino acids, i.e. a total of about 30% by number of the amino acids for a highly acylated collagen.

The acylated collagen, for example succinylated collagen, activated for example with ethyl chloroformate, and the activated subunit, constitute novel reaction intermediates.

Step $d_1$ consists in reacting the activated collagen with a "cysteic" residue containing a blocked thiol group or groups, and step $d_2$ consists in reacting the collagen with an activated spacer compound/cysteic residue subunit, to give an inert precursor of the intended modified collagen.

As far as the present invention is concerned, "cysteic" residues are understood as meaning any compound of the general formula

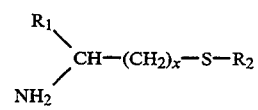

in which:
$R_1$ = H or $COOR'_1$, where R' is an aliphatic and/or aromatic and/or cyclic hydrocarbon chain, preferably an alkyl, alkylene, aryl or aralkylene chain and particularly preferably a methyl, ethyl or allyl chain;

$R_2$ is an aliphatic and/or aromatic and/or cyclic hydrocarbon chain optionally containing sulfur and preferably selected from the groups of the following general formula:

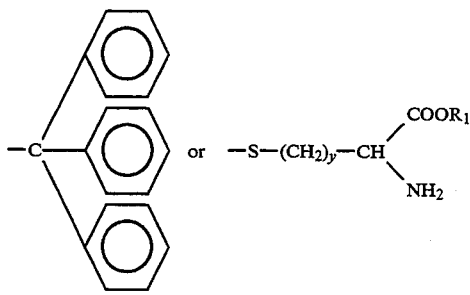 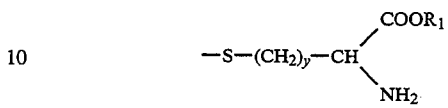

where y=1 or 2; and
x is equal to 1 or 2.

In method I, the substituent $R_2$ constitutes a means of protecting the thiol groups of cysteic residues so as to prevent said thiol groups from reacting with the activated COOH groups of the collagen when they are brought into contact.

According to a preferred provision of the present invention, the cysteic residue used in method I is cystine dimethyl ester:

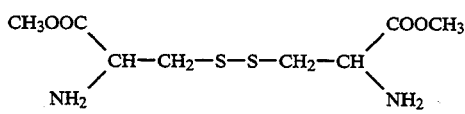

or S-triphenylmethylcysteine methyl ester:

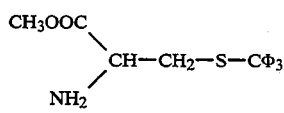

where

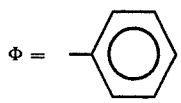

The collagen substituted by the cysteic residue or by the spacer compound/cysteic residue subunit constitutes an inert precursor of the modified collagen which it is desired to obtain. It is a novel stable reaction intermediate.

Steps $e_1$ and $e_2$ of the process according to the invention consist in reconstituting the thiol groups by elimination of the protecting group. Said elimination can be effected by reduction with a reducing agent preferably selected from mercaptans and/or reducing salts and/or organic reducing compounds.

The mercaptan can be mercaptoethanol, mercaptoacetic acid, mercaptoethylamine, benzylmercaptan, thiocresol or dithiothreitol, this last compound being particularly preferred.

Sodium borohydride or sodium bisulfite, for example, can be chosen as the reducing salt.

Phosphines, such as tributylphosphine, are suitable as organic reducing compounds.

It is possible to use mixtures of reducing agents, for example a mercaptoethanol/sodium borohydride combination.

The reduction can be carried out in a basic or neutral aqueous medium, in organic solvents or in mixtures of organic solvents, in the presence or absence of water.

These reduction steps $e_1$ and $e_2$ are performed in particular when the group $R_2$ of the cysteic residue in question is of the type where y=1 or 2.

Steps $e_{11}$ and $e_{21}$ consist in oxidizing the inert precursor with an oxidizing agent such as iodine in alcoholic solution, for example methanolic solution, in a reaction medium based on an aprotic organic polar solvent characteristic of the process according to the invention, such as DMF. Collagen crosslinked by disulfide bridges is obtained.

To obtain the crosslinkable collagen containing free or substituted SH groups, step $f_{11}$ or $f_{21}$ should be carried out in order to reduce this crosslinked collagen.

This reduction is of the type carried out in step $e_1$ or $e_2$ described above.

Steps $e_1$ and $f_1$ are carried out when the inert precursor contains a cysteic residue having a substituent $R_2$ of the $C\Phi_3$ type.

According to another feature, the invention further relates to a process for the production of a crosslinked collagen which is insoluble in water and/or in aprotic polar organic solvents, said process consisting in carrying out steps a, b, c, d and $e_1$ or $e_{21}$ of the process described above.

The cysteic SH residues grafted on to the collagen chains are oxidized to give disulfide bridges between these molecules. This reaction leads to the formation of a three-dimensional network which is insoluble in physiological media and soluble in reducing media capable of reducing disulfide bridges.

The number of bonds formed between these different molecules depends on the degree of substitution and the oxidation conditions.

The degree of crosslinking is decisive as regards the mechanical strength and the kinetics of biodegradability of the crosslinked products obtained.

The crosslinkable collagen and crosslinked collagen according to the invention only contain molecules or derivatives of a biological nature which are capable of being metabolized easily to give compounds recognized as metabolites by animal organisms.

The reagents used during the chemical modifications are either convertible to non-toxic products or can easily be eliminated by non-denaturing processes such as, for example, dialysis.

The modified collagen in reduced form does not contain residual activated groups and the oxidized crosslinked collagen can only contain unreacted thiol groups. These groups are not toxic since they are naturally present in a large number of animal proteins.

The oxidation processes require neither toxic substances nor conditions aggressive towards living tissues.

The invention offers the very appreciable possibility of being able to control all the collagen crosslinking phenomena, including especially the kinetics and the degree of crosslinking. This is particularly useful for the production of molded or extruded objects of the types comprising implants, prostheses, contact lenses, etc.

Another considerable advantage of the invention is that it enables the mechanical properties to be modulated by controlling the number of cysteic residues introduced per unit mass of collagen. It is also possible precisely to target a class of crosslinked products corresponding to the specification sheet established as a function of the intended application and defining the mechanical stresses and the desired biodegradation kinetics.

The products and processes according to the invention have immediate applications on the one hand in human or veterinary medicine and on the other hand in the field of biology.

In human or veterinary medicine, the products can be implants, for example ophthalmological implants, prostheses, for example bone prostheses, dressings in the form of films or felts, artificial tissues (epidermis, vessels, ligaments, bones), encapsulation systems (microspheres, microcapsules) for the controlled release of active principles in vivo, bioencapsulation systems, coverings for rendering implantable medical articles biocompatible, or else suture threads. These products can also be associated with mineral fillers (hydroxyapatite, powdered coral, etc.) so that they can be used as agents for making up bone or cartilage.

In biology, the materials according to the invention constitute excellent supports for two-dimensional cell cultures (films) and three-dimensional cell cultures (felts).

The crosslinked collagen according to the invention can be used by itself or in a mixture with modified or unmodified biological polymers or with synthetic polymers.

Other valuable applications of the products according to the invention pertain to the field of adhesion, e.g. adhesive articles and/or biomaterials and biological or surgical glues.

Further advantages, variants and application possibilities of the present invention are clearly apparent from the Examples which follow.

EXAMPLES

EXAMPLE 1:

Synthesis of collagen-succinyl-cysteinyl in crosslinked form and in crosslinkable form from atelocollagen (steps $a_1$ to $d_1$, $e_{11}$ and $f_1$) (method I)

Step $a_1$: Solubilization of the starting atelocollagen:

32 g of succinic acid are dissolved in 270 ml of methanol. 25 g of atelocollagen (bovine origin—type I+III—supplied by SAOUC) are suspended in this solution. After swelling for 1 h, 290 ml of DMSO or 375 ml of NMP are added and the medium is stirred at 20° C. until dissolution is complete. The medium is then filtered on a 45 μm filter and the methanol is evaporated off under reduced pressure (about 0.3 mbar).

Step $b_1$: Activation and carboxylation of the solubilized collagen:

30 g (300 mmol) of succinic anhydride are added to the methanol-free collagen solution obtained at the end of step $a_1$, and then, when dissolution is complete, 75 ml (538 mmol) of freshly distilled triethylamine are added dropwise over 10 min. The temperature is maintained at 25° C. by an external temperature regulating system. The solution obtained is stirred for 3 to 15 hours and the succinylated collagen is then precipitated by the addition of two volumes of ethyl acetate. The precipitate is then washed with two successive baths of 250 ml of acetone. The solid residue obtained is dissolved in 300 ml of distilled water brought to pH 6.5, after which the solution is dialyzed against distilled water brought to pH 2 (acidification with 6N HCl). 21.5 g of collagen succinylated on 20% of the amino acids are obtained after lyophilization.

The degree of succinylation is determined by two techniques:
enzymatic determination of the succinic acid after hydrolysis of the collagen in an acid medium, and potentiometric determination of the carboxyl groups.

Steps $c_1$ and $d_1$: Activation of succinylated atelocollagen and grafting of S-triphenylmethylcysteine ethyl ester:

4 g of 20% succinylated collagen (total acidity 10.54 mmol) obtained in the previous step are dissolved in 80 ml of anhydrous DMF. After total dissolution, 1.72 ml of triethylamine (12 mmol) are added, with vigorous stirring. The reaction medium is cooled to −5° C. before the dropwise addition of 1.92 ml of ethyl chloroformate (20 mmol). After 15 min, the succinylated collagen is activated and step $c_1$ is complete.

Step $d_1$ is initiated by the addition to the reaction medium of 7.2 g of S-triphenylmethylcysteine methyl ester (18 mmol) obtained by bringing cysteine methyl ester into contact with triphenylmethanol and $BF_3$ etherate (temperature above 50° C.). The reaction medium is then stirred for 16 h at 20°–25° C. The collagen derivative formed is subsequently precipitated by the addition of 400 ml of ethyl acetate. After redissolution in DMF and reprecipitation with ethyl acetate, the collagen derivative obtained is washed with methanol and then dried under reduced pressure at 20°–25° C. to give 4.5 g of dry product.

Steps $e_1$ and $f_{11}$: Deblocking of the protecting group—"CΦ$_3$"—and preparation of collagen crosslinked by disulfide bridges:

The 4.5 g of product formed in step $d_1$ are stirred for 3 h in 45 ml of DMF. The derivative is entirely solubilized at this stage. 1.45 g (7 mmol) of iodine solubilized in 20 ml of methanol are added.

A gel is formed. The medium is left to stand for 18 h and then washed several times with a water/acetone mixture (50/50 v/v) until decolorization is complete. After three washes with ethyl acetate, the product is dried to give 3.46 g of dry final derivative.

The degree of substitution of the collagen obtained is of the order of 3 to 5 cysteine residues per 100 amino acids according to determination of the thiol groups with DTNB.

This crosslinked derivative can be reduced with dithiothreitol to give the collagen thiol derivative, which can easily be crosslinked with air, hydrogen peroxide or iodine.

EXAMPLE 2

Synthesis of collagen-succinyl-cysteinyl in crosslinked form and in crosslinkable form from a succinyl salt of atelocollagen (method I)

Preliminary step: Preparation of the succinyl salt of atelocollagen:

12 g of succinic acid (102 mmol) are dissolved in 225 ml of isopropanol. 12 g of atelocollagen are added to this reaction medium, which is stirred magnetically for 2 h at 20°–25° C.

After filtration on a 50 μm sieve, the collagen fibers are drained and then washed twice with 150 ml of isopropanol before being sieved again.

13 g of dry succinyl salt of atelocollagen are then recovered after drying for 4 h under reduced pressure at 25°–30° C.

Steps $a_1$ and $b_1$: Solubilization of the salt and synthesis of succinylated atelocollagen from its succinyl salt:

10 g of succinyl salt of atelocollagen are dissolved in 240 ml of a DMF/DMSO mixture (60/40 v/v), with magnetic stirring. 3.9 g of succinic anhydride (39 mmol) are added to the medium, together with 8.7 ml of freshly distilled triethylamine (62.5 mmol). The reaction medium is left to stand for 24 h at 20°–25° C., with magnetic stirring, and then dialyzed against distilled water. After acidification to pH 2–4, the product is precipitated with acetone before being dialyzed against water at pH 2. 8 g of dry 9.5% succinylated derivative (determination by potentiometry) are obtained after lyophilization.

Steps $c_1$ and $d_1$: Activation of succinylated atelocollagen and grafting of S-triphenylmethylcysteine methyl ester:

4.5 g of 9.5% succinylated atelocollagen (total acidity 8.37 mmol) are dissolved in 90 ml of anhydrous DMF for 18 h at 20°–25° C., with magnetic stirring. After the medium has been cooled to $-5°/-10°$ C., 1.575 ml of triethylamine (11.3 mmol) are added and 1.2 ml of ethyl chloroformate (12.6 mmol) are then added dropwise.

After stirring for 15 min at $-5°/-10°$ C., the succinylated collagen is activated and step $c_1$ is complete.

Step $d_1$ is initiated by the addition of 6.8 g (16.5 mmol) of S-triphenylmethylcysteine methyl ester to the reaction medium, which is left to stand for 1 h at $-5°$ C., with magnetic stirring, and then for 16 h at 20°–25° C.

The derivative formed is then precipitated with 400 ml of ethyl acetate. After redissolution in DMSO and reprecipitation in ethyl acetate, the derivative is washed with methanol and then dried under reduced pressure to give 7.6 g of dry product.

Steps $e_{11}$ and $f_{11}$: Deblocking of the protecting group—"CΦ$_3$"—and preparation of collagen crosslinked by disulfide bridges:

The 7.6 g of product formed in step $d_1$ are stirred for 3 h in 80 ml of DMF. 100 ml of methanol are added. The derivative is totally solubilized at this stage. 1.77 g (7 mmol) of iodine solubilized in 20 ml of methanol are then added.

A gel is formed. The medium is left to stand for 18 h and then washed several times with a water/acetone mixture (50/50 v/v) until decolorization is complete. After three washes with ethyl acetate, the product is dried to give 6 g of dry final derivative.

The degree of substitution of the modified collagen obtained is estimated to be 11 cysteine residues per 100 amino acids according to determination of the thiol groups with DTNB.

This crosslinked derivative can be reduced with dithiothreitol to give the collagen thiol derivative, which can easily be crosslinked with air, hydrogen peroxide or iodine.

EXAMPLE 3

Synthesis of collagen-succinyl-cysteinyl (crosslinked and crosslinkable) from type I+III bovine collagen with telopeptides (method I)

Steps $a_1$ and $b_1$:

2.5 g of type I+III bovine collagen with telopeptides are dissolved at 50° C. in 80 ml of water and the fluid solution obtained is stirred at this temperature for 1 h. 0.25 g of dithiothreitol (1.11 mmol) is then added after the collagen solution has been cooled to about 30° C., and the pH is brought to 9.5 with sodium hydroxide. The solution obtained is stirred for 1 h and then brought to pH 2.5–3 with hydrochloric acid. The collagen is then precipitated with two volumes of acetone, washed in the same solvent and then harvested by filtration and dried under reduced pressure.

The powdered collagen obtained previously (2.2 g) is suspended in 20 ml of methanol and stirred for 15 min and 40 ml of anhydrous dimethyl sulfoxide containing 0.4 g of succinic acid.(3.29 mmol) are then added. After stirring for 30 min, the methanol is evaporated off under reduced pressure at 30° C. 2.91 g (29.1 mmol) of succinic anhydride are added to the solution obtained, followed, after dissolution of the succinic anhydride, by 4.5 ml (32.3 mmol) of freshly distilled triethylamine. The medium is stirred for 2 h at 20° C. The succinylated collagen is precipitated with 200 ml of acetone and then harvested by filtration. The precipitate is then dissolved in 80 ml of water at pH 8, the solution is centrifuged for 20 min at 15,000 g and the supernatant is dialyzed against distilled water maintained at a pH of about 2 with hydrochloric acid. The dialyzate is lyophilized to give 2.3 g of succinylated collagen having a degree of substitution of 18% according to determination by potentiometry.

Steps $c_1$, $d_1$ and $e_1$:

1 g of 18% succinylated bovine collagen (about 2.52 mmol of carboxyl groups) is solubilized in 25 ml of anhydrous DMSO. 0.55 g (3.39 mmol) of powdered carbonyldiimidazole is added to this very viscous solution. The medium is degassed under reduced pressure and stirred for 45 min. The addition of 0.8 g (2.35 mmol) of cystine dimethyl ester dissolved in 5 ml of anhydrous DMSO gives a gel in a few minutes and this gel is left to stand for 18 h in the dark. It is dispersed in 100 ml of acetone, stirred for 2 h and then washed in several baths of acetone, harvested by filtration and dried under reduced pressure.

The modified collagen obtained (1 g) is suspended in 50 ml of water maintained at pH 9.5. A solution of 0.4 g (2.6 mmol) of dithiothreitol in 10 ml of water at pH 9.5 is added and the medium is stirred for 18 h at 20°–25° C. The solution obtained is centrifuged for 15 min at 15,000 g, the supernatant is acidified to pH 1.8 and the gel obtained is dialyzed against distilled water at pH 1.5–1.8. The dialyzate is lyophilized to give 0.985 g of modified collagen with a degree of substitution of about 9 thiol groups per 100 amino acids of the starting collagen.

EXAMPLE 4

Synthesis of collagen-succinyl-cysteamine from type I+III bovine collagen with telopeptides (method I)

The protocol is identical to that of Example 3.

1.05 g of thiolized collagen are obtained from 1 g of succinylated collagen. The grafting rate is estimated to be 14% based on the amino acids of the starting collagen.

EXAMPLE 5

Synthesis of collagen-succinyl-cysteaminyl from collagen with telopeptides and a disuccinylcystamine reaction subunit (method II)

2.2 g of acid-soluble collagen (about 0.78 mmol of lysyl residues) are stirred for 15 min in 75 ml of methanol, after which 125 ml of dimethyl sulfoxide are added. The mixture is stirred at 40° C. for 15 min and the methanol is then evaporated off under reduced pressure. 0.707 g (1.564 mmol) of the diimidazolide of disuccinylcystamine (obtained by reacting succinic anhydride with cystamine in a basic aqueous medium) is dissolved in 20 ml of DMSO and the solution obtained is added to the collagen solution. The mixture is stirred at 20°-25° C. for 20 h and the gel obtained is then dispersed in 200 ml of acetone, washed with 2×100 ml of this solvent and then washed over 2 h with 2×500 ml of water maintained at pH 7-9.5 with sodium hydroxide.

The gel is harvested by filtration and then placed in 50 ml of an aqueous solution of dithiothreitol (0.5 g, 3.25 mmol) adjusted to pH 9.5 with sodium hydroxide. After stirring for 18 h at 20°-25° C., the medium is heated at 40° C. for 15 min and then centrifuged at 15,000 g for 10 min. The supernatant is then acidified to pH 1.8 and dialyzed against water at the same pH. The collagen medium is then lyophilized to give 1.8 g of collagen thiolized on 3% of the amino acids of the starting collagen.

EXAMPLE 6

Synthesis of collagen-succinyl-cysteaminyl from type I+III bovine atelocollagen (method I)

10 g of 18% succinylated atelocollagen (about 25 mmol of carboxyl groups) are dissolved in 150 ml of anhydrous dimethyl sulfoxide. The viscous solution obtained is degassed under reduced pressure and 9.1 g (56 mmol) of powdered carbonyldiimidazole are then added all at once at a temperature of 20°-25° C. After the carbonyldiimidazole has dissolved, the solution obtained is degassed under reduced pressure for 1 to 2 h. 7.6 g (33.77 mmol) of cystamine hydrochloride are dissolved at 40° C. in 50 ml of anhydrous DMSO and the solution obtained is added all at once to the solution of activated collagen, with vigorous stirring. The gelled medium which is obtained in a few minutes is left to stand for 3-24 h at 20°-25° C. The gel is then dispersed in 400 ml of ethyl acetate, recovered by filtration and then washed twice in 300 ml of acetone. The granular product obtained is then dispersed for 16 h in water maintained at pH 10 with sodium hydroxide, and is subsequently harvested by filtration. The product obtained is suspended in 90 ml of water at pH 10, after which a solution of 3.85 g (25 mmol) of dithiothreitol in 20 ml of water at pH 10 is added. The mixture obtained is stirred for 16 h at 20° C. and centrifuged at 15,000 g for 15 min.

The supernatant is acidified to pH 1.8 with hydrochloric acid and then dialyzed against water at pH 1.5-2. The dialyzate is lyophilized to give 10.7 g of thiolized collagen. Determination of the thiol groups by the DTNB method indicates a degree of substitution of 15% based on the amino acids of the collagen, i.e. a degree of substitution of about 55% based on the carboxyl groups of the starting succinylated collagen.

EXAMPLE 7

Synthesis of collagen-succinyl-cysteinyl from type I+III bovine atelocollagen (method I)

10 g of 18% succinylated atelocollagen are activated under the same conditions as in Example 6. 8.5 g (25 mmol) of cystine dimethyl ester are dissolved in 10 ml of anhydrous DMSO and the solution obtained is then added to the solution of activated collagen. The medium is stirred for 16-60 h at 20°-25° C. The gel obtained is dispersed in three volumes of acetone, with vigorous stirring, washed three times in 150 ml of this solvent and then harvested by filtration. The modified collagen can then be obtained in powder form by evaporation of the residual acetone under reduced pressure, or used directly in the next step.

The modified collagen is suspended in 100 ml of water maintained at pH 9.5 with sodium hydroxide. A solution of 3.85 g (25 mmol) of dithiothreitol in 20 ml of water at pH 9.5 is added to this suspension. The mixture is stirred for 16-24 h at 20-25° C. and centrifuged at 15,000 g for 15 min. The supernatant is acidified to pH 1.8 with hydrochloric acid and then dialyzed against water at pH 1.5-2 until a DTNB test on the dialysis waters is negative. The dialyzate is lyophilized. Determination of the thiol groups by the DTNB method indicates a degree of substitution of about 9% based on the amino acids of the collagen.

EXAMPLE 8

Synthesis of collagen-succinyl-cysteaminyl from atelocollagen (method II)

2.4 g of type I+III bovine atelocollagen (about 0.855 mmol of lysyl residues) are dissolved in 30 ml of anhydrous DMSO by the method described in Example 3, step b$_1$.

0.6 g (1.7 mmol) of disuccinylcystamine is dissolved in 20 ml of dimethylformamide to which 0.55 g (3.41 mmol) of powdered carbonyldiimidazole is added. The solution is degassed under reduced pressure and stirred for 2 h.

The heterogeneous medium obtained is added to the collagen solution obtained previously and the resulting solution is stirred at 20°-25° C. for 18 h. The collagen is then precipitated by the addition of three volumes of acetone and collected by filtration. The precipitate is then dispersed in 200 ml of water maintained at acid pH and the suspension is stirred for 18 h.

The washed precipitate is dispersed in 50 ml of water maintained at pH 10 with sodium hydroxide. A solution of 0.26 g (1.7 mmol) of dithiothreitol in 5 ml of water at pH 10 is added to the suspension obtained. The medium is stirred for 24–48 h at 20°-25° C. and acidified to pH 1.8 with hydrochloric acid and the gel obtained is dialyzed against water at pH 1.5-2 and then lyophilized to give 2.3 g of modified collagen. Determination of the thiol groups by the DTNB method indicates a degree of substitution of 3.1% based on the amino acids of the starting collagen, which corresponds to a degree of substitution of about 100% of the lysyl residues.

EXAMPLE 9

Synthesis of collagen-succinyl-cysteinyl from atelocollagen (method I)

4 g of atelocollagen (about 1.42 mmol of lysyl residues) are dissolved in DMSO according to the protocol described in Example 2. 0.7 g (3 mmol of carboxyl groups) of disuccinylcystine dimethyl ester is dissolved in 10 ml of DMSO, after which 0.486 g (3 mmol) of carbonyldiimidazole is added. The solution is stirred and degassed under reduced pressure for 1 h and is then added to the collagen solution. After standing for 72 h at 20°-25° C., the reaction medium is dispersed in 300 ml of acetone and the solid phase is washed for 1 h in 200 ml of acetone and then for 2×1 h in 500 ml of water maintained at pH 9-9.5 with sodium hydroxide. The gel is harvested by filtration and then dispersed in 70 ml of water at pH 9.5.

An aqueous solution of dithiothreitol (6 ml, 0.7 g, 4.54 mmol) at pH 9.5 is added to this suspension. After a reaction time of 18 h, the medium is heated for 10 min at 30°° C. and then centrifuged for 15 min at 15,000 g. The supernatant is treated as in Example 7 to give 3.9 g of collagen thiolized on 2.4–2.8% of the amino acids of the starting collagen.

OXIDATION-CROSSLINKING OF THE THIOLIZED COLLAGENS

All the thiolized collagens are oxidizable and crosslinkable in the presence of oxidizing agents. Depending on the conditions of oxidation of the collagens in solution (aqueous, organic or mixed solution, temperature, ionic strength, pH, concentration) and the nature of the oxidizing agent, crosslinking results in the formation of a gel or a precipitate by variation of the viscosity of the solution.

Among the oxidizing agents used, there may be mentioned oxygen by itself, oxygen in the presence of ultraviolet radiation, hydrogen peroxide in an acidic, neutral or basic medium, and iodine in alcoholic or aqueous solution. Crosslinking can also be carried out on non-solubilized thiolized collagen in the form of films or powders, for example by immersion in oxidizing solutions.

All the oxidized collagens are insoluble in aqueous and organic media, but can be solubilized in reducing solutions at basic pH, for example an aqueous solution of dithiothreitol at pH 9.5.

EXAMPLE 10

Formation of a gel 0.5 g (containing about 0.16 mmol of thiol groups) of atelocollagen produced in Example 8 is dissolved at 40° C. in 10 ml of water and the solution is then brought to pH 7 with sodium hydroxide and pH 8.2 with 1M carbonate buffer of pH 9. The solution is filtered on a 0.22 micrometer filter and then gelled by lowering of the temperature.

The thermoreversible gel obtained is immersed in 150 ml of 0.15M sodium borate buffer of pH 8.2, containing 0.15% of hydrogen peroxide, and kept in this solution for 6 to 24 h, with gentle stirring. The transparent gel obtained is then washed in several baths of water and can be stored in a 25% aqueous solution of ethanol.

This gel is no longer thermoreversible and no longer contains free thiol groups.

EXAMPLE 11

Formation of a film 0.7 g of collagen produced in Example 8 (containing about 0.23 mmol of thiol groups) is dissolved at 40° C. in 50 ml of water and the solution is then brought to pH 8.2 as in Example 10. After filtration on a 0.22 micrometer filter, the solution is run on to a 120×120 mm polystyrene box and evaporated in the open air at 20°–25° C. The film obtained is then immersed in 100 ml of a solution of hydrogen peroxide (Example 10) for 1 to 5 h and subsequently washed with water. This film can be stored in the dry state or in a 25% aqueous solution of ethanol.

EXAMPLE 12

Ex vivo evaluation of tissue adhesion

The evaluation of the adhesive properties of the products according to the invention was carried out on rabbit muscular tissues (back). These tissues are kept at 4° C. in a physiological salt solution for 48 hours maximum. The rabbit tissue is cut along the fibers with the aid of an electrical cutter (dimensions in mm :2.5×25×25).

The tests are carried out using a standard traction machine, for example an Adamel Lhormargy DY34, fitted with a force gauge of 100N. This machine allows us to obtain the force-displacement curve from which the ultimate adhesive strength (in tensile mode), the adhesive energy (from the area under the curve) can be calculated.

in each type of test, two test specimens of rabbit tissue are both stuck with a cyanoacrylate glue (for example LOCTITE ® Superglue, liquid or gel form) onto very rigid inert supports, glass or cardboard, of large dimensions. The tests are carried out after a contact time of three minutes and under a pressure of 4N.

A solution of 5% succinylated cysteamine collagen, (prepared as in example 4), is prepared under an inert atmosphere. Its pH is adjusted between 7 and 8. Before the test the surfaces of the tissues are superficially soaked with a BETADINE ® dermic solution, (iodised polyvinylpyrolidone), 100 1 µl of collagen solution is then added between the two tissues. On contact with the iodised solution (oxidant) a progressive gelation can be observed.

After three minutes under a pressure of 4N the tested collagencystine exhibits an adhesive strength of 3;5±1;9N (average after 14 tests) and an adhesive energy of 7;0±3;1 mJ.

These interesting results can be compared to those obtained in the same test for the fibrine glues. Thus, for BIOCOL ® glue (deposit of 200 µl) the adhesive strength is 2;5±1;6N (average after 17 tests) and the adhesive energy of 3;8±2;0 mJ.

What is claimed is:

1. A crosslinkable modified collagen which is soluble in water and/or in aprotic polar organic solvents and which comprises free or unsubstituted thiol groups carried by residues of cysteine, at least some of said residues being fixed to the collagen via spacer compounds.

2. A modified collagen according to claim 1 wherein the spacer compounds are carboxylated hydrocarbon units.

3. A modified collagen according to claim 2 wherein the carboxylated hydrocarbon units come from dicarboxylic acids capable of forming cyclic anhydrides.

4. A modified collagen according to claim 3 wherein the dicarboxylic acids are selected from the group consisting of succinic acid, glutaric acid, phthalic acid, itaconic acid, citraconic acid and maleic acid.

5. A crosslinkable modified collagen which is soluble in water and/or in aprotic polar organic solvents and which comprises free or unsubstituted thiol groups carried by residues of cysteine, at least some of said residues being fixed to the collagen via spacer compounds, wherein the cysteine residues are selected from the group consisting of cysteine, cystine, homocysteine, homocystine, cysteamine and cystamine.

6. An insoluble crosslinked collagen which comprises intercatenary bridging structures which are formed at least partially by disulfide bridges obtained from cysteic residues fixed to the collagen at least partially via spacer compounds.

7. A crosslinked collagen according to claim 6 which is obtained from a crosslinkable modified collagen which is soluble in water and/or in aprotic polar organic solvents and which comprises free or unsubstituted thiol groups carried by residues of cysteine, at least some of said residues being fixed to the collagen via spacer compounds.

8. A process for the production of a stable intermediate of a crosslinkable modified collagen which is soluble in water and/or in aprotic polar organic solvents and which comprises free or substituted thiol groups, said process comprising the following successive steps:
   $a_1$: solubilization of a starting animal or human collagen in at least one aprotic polar organic solvent;
   $b_1$: acylation and carboxylation of the solubilized collagen from step $a_1$;
   $c_1$: activation of free carboxyl groups of the collagen from step $b_1$; and
   $d_1$: reaction of the activated collagen from step $c_1$ with a cysteic residue comprising a blocked thiol Group or groups, or a blocked carboxyl group or groups, to produce a stable intermediate of the intended modified collagen.

9. A process for the production of a crosslinkable modified collagen which comprises steps $a_1$ through $d_1$ as claimed in claim 8, and which further comprises step $e_1$ which is direct activation of the stable intermediate from step $d_1$ by reduction to produce the modified collagen carrying stabilized free or substituted thiol groups.

10. A process for the production of a stable intermediate of a crosslinkable modified collagen which is soluble in water and/or in aprotic polar organic solvents and which comprises free or substituted thiol groups, said process comprising the following successive steps:
    $a_2$: solubilization of a starting animal or human collagen in at least one aprotic polar organic solvent;
    $b_2$: preparation of a subunit comprising a spacer compound and at least one cysteic residue, wherein the subunit carries protected thiol groups;
    $c_2$: activation of free carboxyl groups of the subunit from step $b_2$; and
    $d_2$: reaction of the collagen from step $a_2$ with the subunit from step $c_2$ to produce a stable intermediate of the intended modified collagen.

11. A process for the production of a crosslinkable modified collagen which comprises steps $a_2$ through $d_2$ as claimed in claim 10, and which further comprises step $e_2$ which is direct activation of the stable intermediate from step $d_2$ by reduction to produce the modified collagen carrying stabilized free or substituted thiol groups.

12. An intermediate obtained according to the process of claim 8 or claim 10, said intermediate consisting essentially of collagen which has reacted with a dicarboxylic acid via at least some of the reactive OH and $NH_2$ groups of the collagen, and which comprises from 4 to 22 carboxyl grafts per 100 amino acids.

13. An intermediate according to claim 12 wherein the dicarboxylic acid is succinic acid or glutaric acid.

14. A process for the production of a crosslinked modified collagen which comprises steps $a_1$ through $d_1$ as claimed in claim 8, and which further comprises the following successive steps:
    $e_1$: indirect activation of the stable intermediate from step $d_1$ by oxidation to produce collagen crosslinked via intercatenary disulfide bridges; and
    $f_1$: conversion of the crosslinked collagen from step $e_1$ by reduction to modified collagen carrying stabilized free or substituted thiol groups.

15. A process for the production of a crosslinked modified collagen which comprises steps $a_2$ through $d_2$ as claimed in claim 10, and which further comprises the following successive steps:
    $e_2$: indirect activation of the stable intermediate from step $d_2$ by oxidation to produce collagen crosslinked via intercatenary disulfide bridges; and
    $f_2$: conversion of the crosslinked collagen from step $e_2$ by reduction to modified collagen carrying stabilized free or substituted thiol groups.

16. A biomaterial for use in medicine which comprises a modified collagen according to claim 1.

* * * * *